US011642886B2

(12) United States Patent
Marra, III (10) Patent No.: US 11,642,886 B2
(45) Date of Patent: May 9, 2023

(54) MODIFIED FLUID JET PLUME CHARACTERISTICS

(71) Applicant: Funai Electric Co., Ltd., Osaka (JP)

(72) Inventor: Michael A. Marra, III, Lexington, KY (US)

(73) Assignee: Funai Electric Co., Ltd.

( * ) Notice: Subject to any disclaimer, the term of this patent is extended or adjusted under 35 U.S.C. 154(b) by 48 days.

(21) Appl. No.: 17/225,215

(22) Filed: Apr. 8, 2021

(65) Prior Publication Data

US 2022/0324227 A1 Oct. 13, 2022

(51) Int. Cl.
*B41J 2/14* (2006.01)
*B41J 2/16* (2006.01)

(52) U.S. Cl.
CPC ............ *B41J 2/1433* (2013.01); *B41J 2/162* (2013.01); *B41J 2/1626* (2013.01)

(58) Field of Classification Search
CPC ......... B41J 2/1433; B41J 2/162; B41J 2/1626
See application file for complete search history.

(56) References Cited

U.S. PATENT DOCUMENTS

| | | | |
|---|---|---|---|
| 5,811,019 A | 9/1998 | Nakayama et al. | |
| 6,142,607 A | 11/2000 | Takata et al. | |
| 7,014,297 B2 | 3/2006 | Miki et al. | |
| 7,448,710 B2 | 11/2008 | Kusunoki | |
| 8,007,079 B2 | 8/2011 | Takahashi | |
| 8,684,498 B2 | 4/2014 | Kuwata | |
| 9,227,403 B2 | 1/2016 | Yokoyama et al. | |
| 9,969,166 B2 | 5/2018 | Suzuki | |
| 10,252,526 B2 | 4/2019 | Tamai | |
| 2007/0000785 A1* | 1/2007 | Drury | C25D 1/08 427/586 |
| 2011/0297146 A1* | 12/2011 | Tanaka | A61M 15/025 128/200.14 |
| 2013/0070025 A1* | 3/2013 | Kuwata | B41J 2/14274 239/548 |
| 2013/0288183 A1* | 10/2013 | Ishikawa | G03F 7/2022 430/320 |

* cited by examiner

*Primary Examiner* — Jason S Uhlenhake
(74) *Attorney, Agent, or Firm* — Luedeka Neely Group, PC (57) ABSTRACT

A fluid jet ejection device, a method of making a fluid jet ejection head, and a method of improving the plume characteristics of fluid ejected from the fluid jet ejection head. The pharmaceutical drug delivery device includes a cartridge body; and a fluid jet ejection cartridge disposed in the cartridge body. The fluid jet ejection cartridge contains a fluid and an ejection head attached to the fluid jet ejection cartridge. The ejection head contains a plurality of fluid ejectors thereon and a nozzle plate having a plurality of fluid ejection nozzles therein associated with the plurality of fluid ejectors. At least one of the plurality of fluid ejection nozzles has an orthogonal axial flow path relative to a plane defined by the nozzle plate and at least one of the plurality of fluid ejection nozzles has an angled axial flow path relative to a plane define by the nozzle plate.

11 Claims, 8 Drawing Sheets

MODIFIED FLUID JET PLUME CHARACTERISTICS

TECHNICAL FIELD

The disclosure is directed to fluid jet ejection devices for delivering fluid mist droplets therefrom and in particular to modified fluid jet plume characteristics for the fluid jet ejection devices.

BACKGROUND AND SUMMARY

Fluid ejection devices have been designed and used to eject ink onto a substrate. However, new uses for fluid ejection devices continue to evolve. For example, fluid ejection devices may be used for vapor producing devices for drug delivery, such as nasal, oral, pulmonary, ophthalmic, and wound care application, and for ejecting a variety of non-aqueous fluids such as lubricants and fragrances. Many of the foregoing applications require that a droplet mist be ejected from the fluid ejection device. However, conventional fluid ejection devices are designed to eject fluid droplets in a straight line toward a substrate. Using a fluid ejection device to provide a mist of fluid droplets is antithetical to the design of conventional fluid ejection devices.

For example, nasal spray devices provide a mist of fluid that is injected into the nasal cavity. Nasal spray devices have become important methods for delivering drugs to patients. Such devices are more convenient to use than the administration of drugs through intravenous (IV) or injection. Spray devices also provide higher bioavailability of drugs compared to oral administration of drugs. The absorption of drugs through spray devices is more rapid compared to the absorption of drugs administered orally since drugs delivered by nasal spray devices directly enter the blood stream making their effect more immediate.

Figure 1:
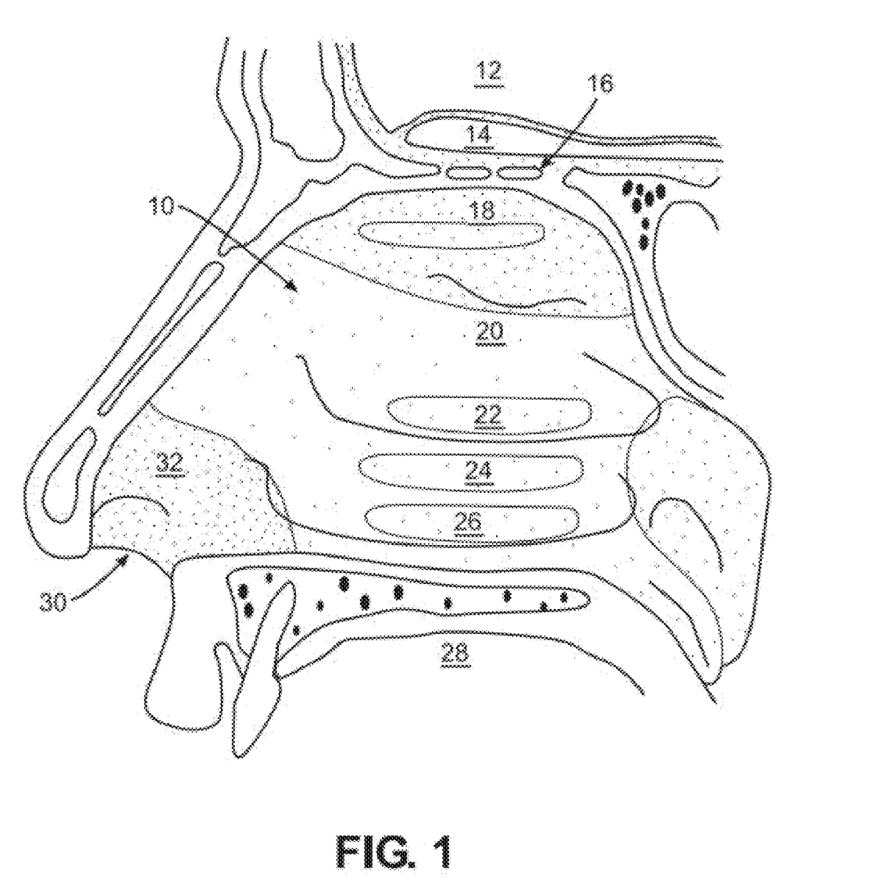
FIG. 1 is a cross-sectional representation, not to scale, of a portion of a nasal cavity and scull of a person.
Figure 2:
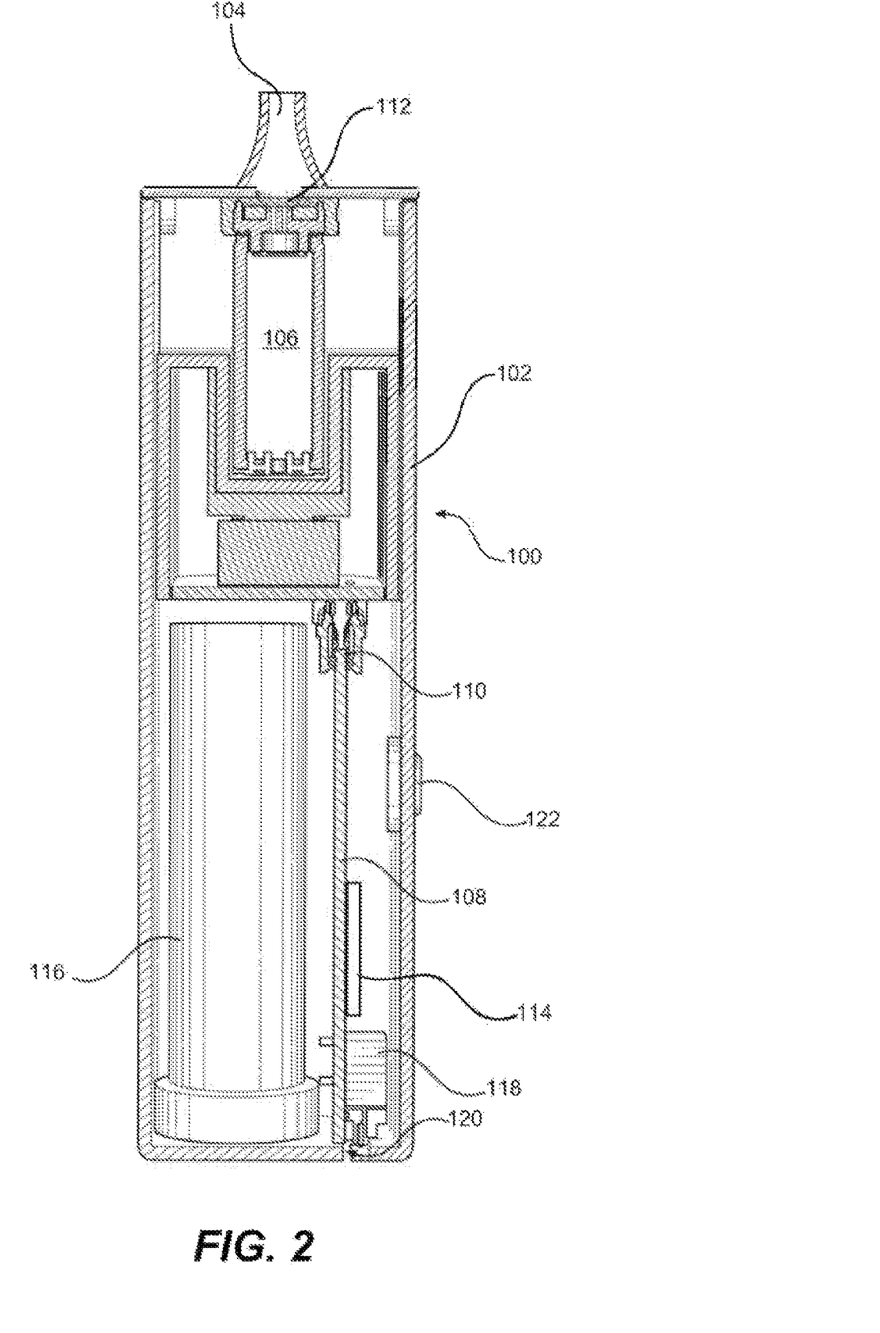
FIG. 2 is a cross-sectional view, not to scale of a pharmaceutical drug delivery device according to an embodiment of the disclosure.
Figure 3:
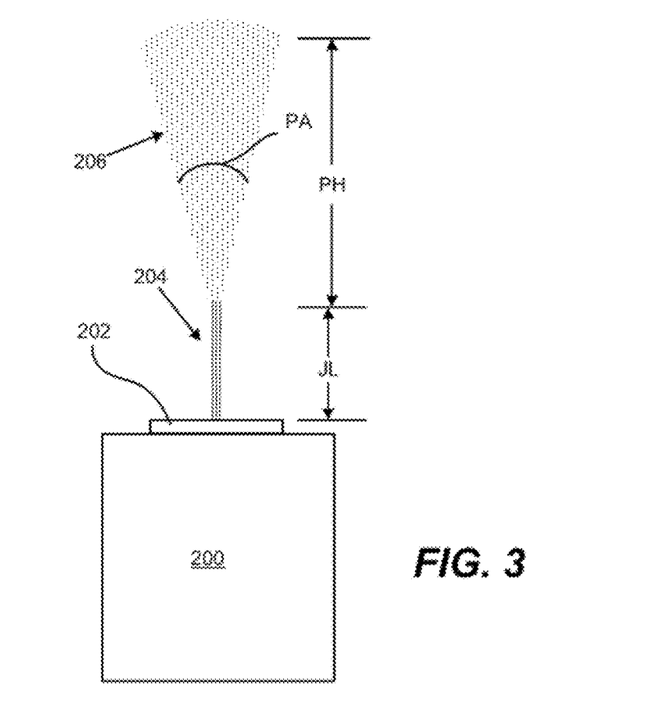
FIG. 3 is a schematic illustration of an ejection device showing a fluid jet stream and a droplet plume generated by fluid droplet ejection from an ejection head.
Figure 4:
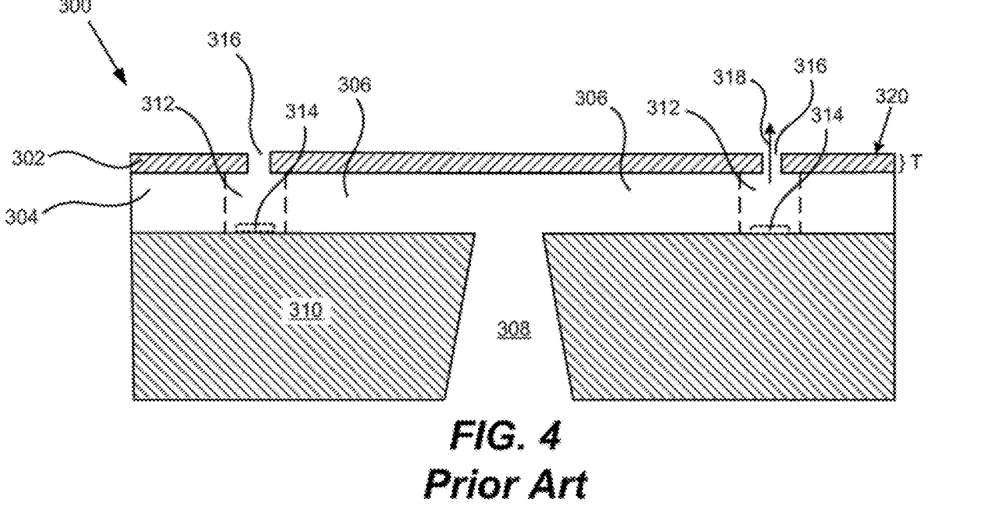
FIG. 4 is a schematic cross-sectional view, not to scale, of a portion of a prior art ejection head.
Figure 5:
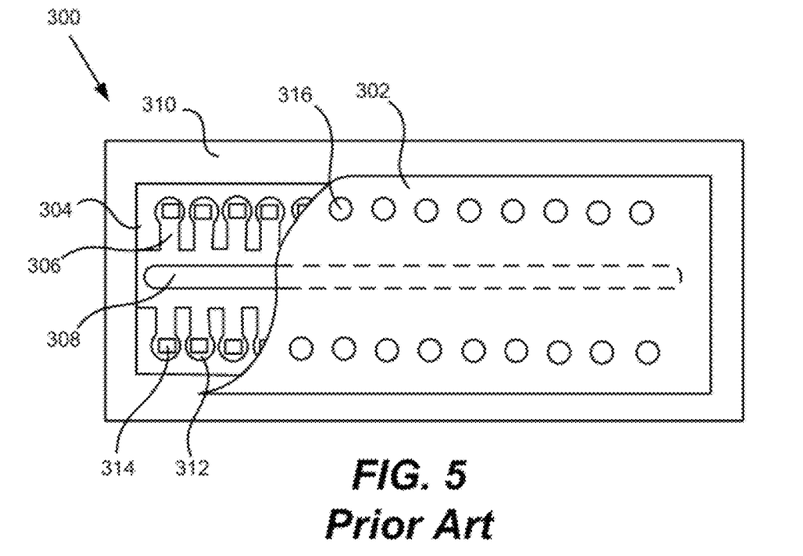
FIG. 5 is a plan view, not to scale, of a prior art ejection head and nozzle plate showing details of a flow feature layer on a semiconductor substrate.
Figure 6:
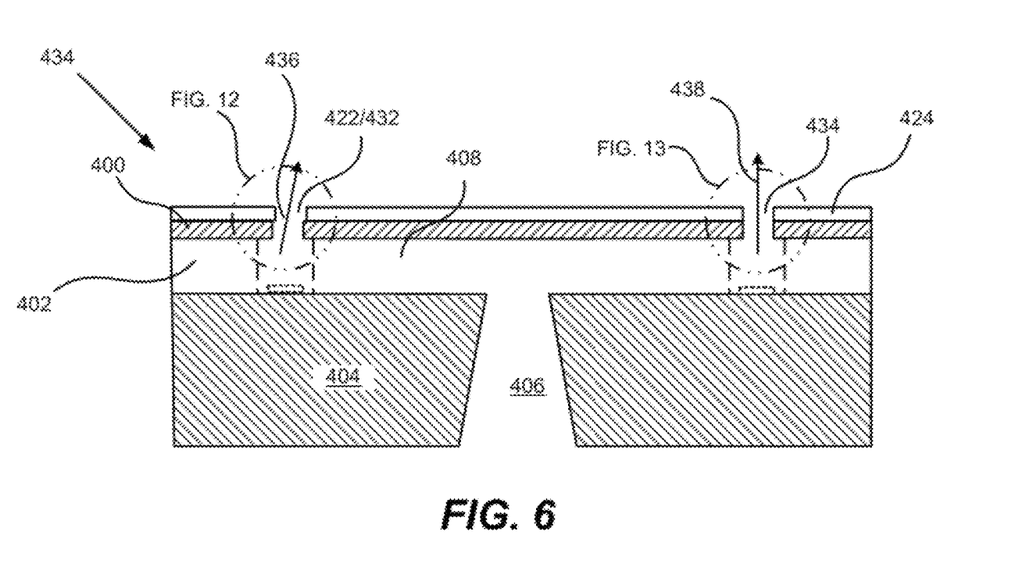
FIG. 6 is a schematic cross-sectional view, not to scale, of a portion of an ejection head according to the disclosure.
Figure 7:
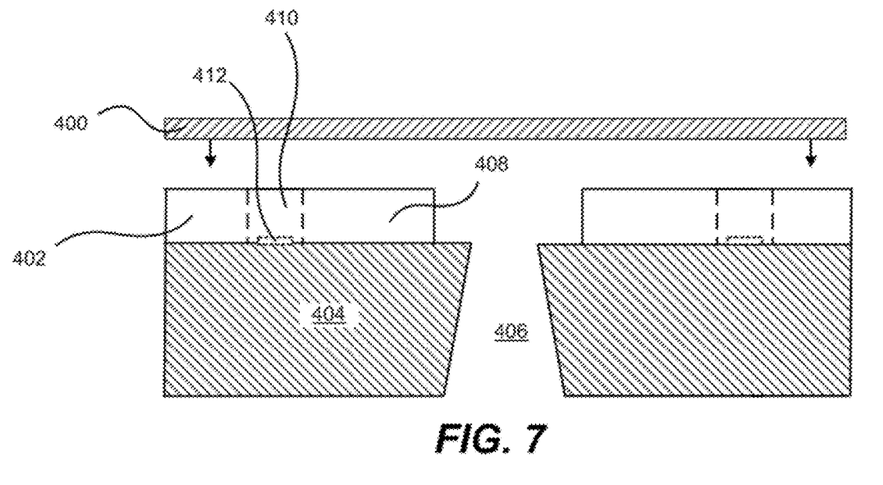
FIGS. 7-10 are schematic illustrations of a process for making an ejection head according to an embodiment of the disclosure.
Figure 8:
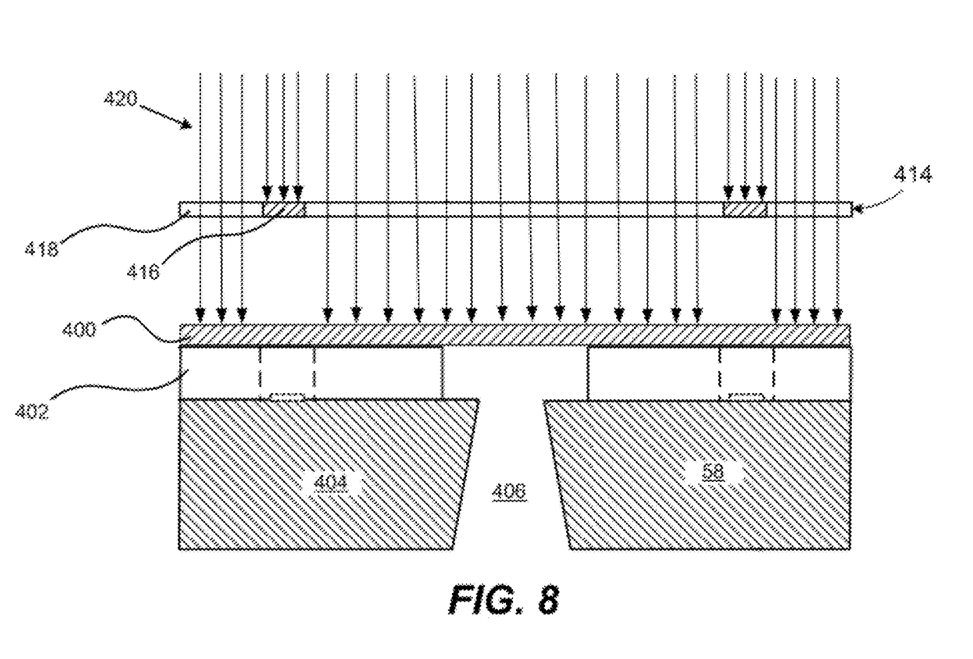
Figure 9:
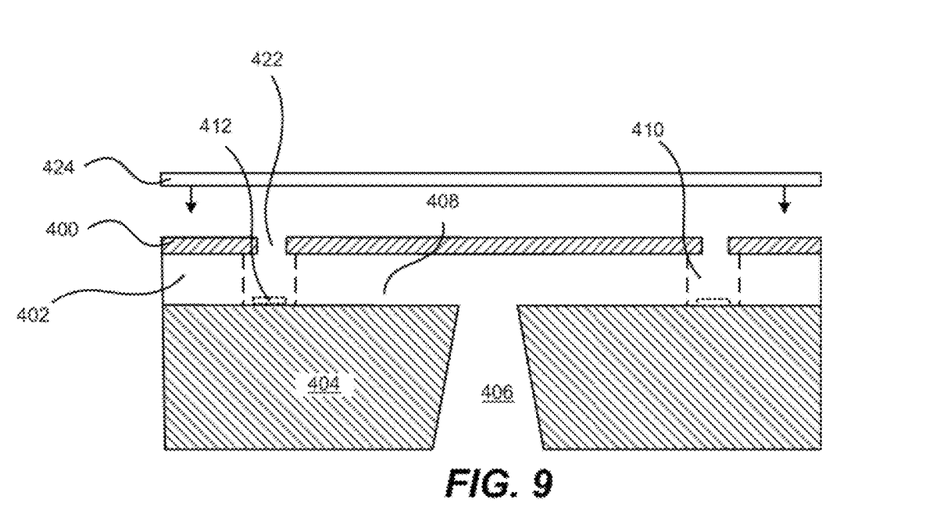
Figure 10:
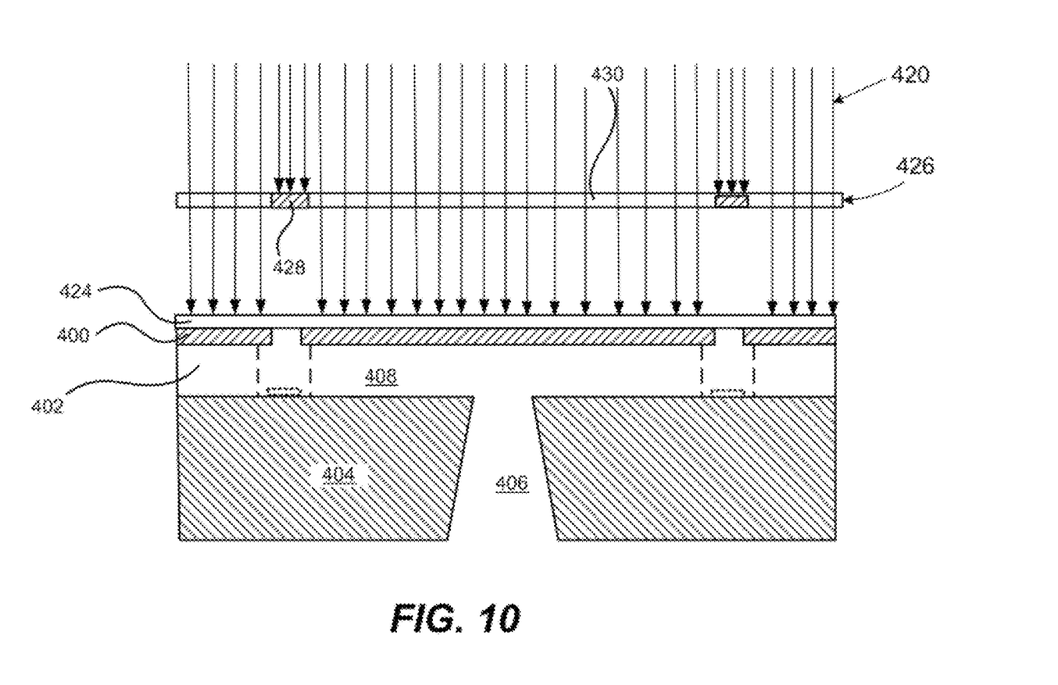
Figure 11:
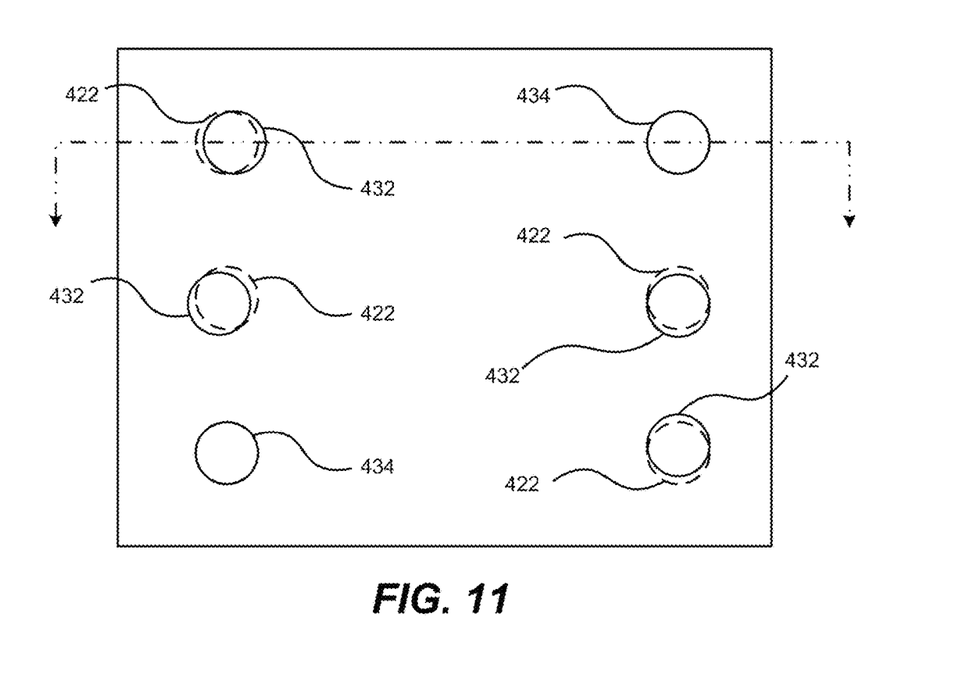
FIG. 11 is a plan view of a portion of a nozzle plate, not to scale, showing offset nozzle holes through first and second nozzle plate layers.
Figure 12:
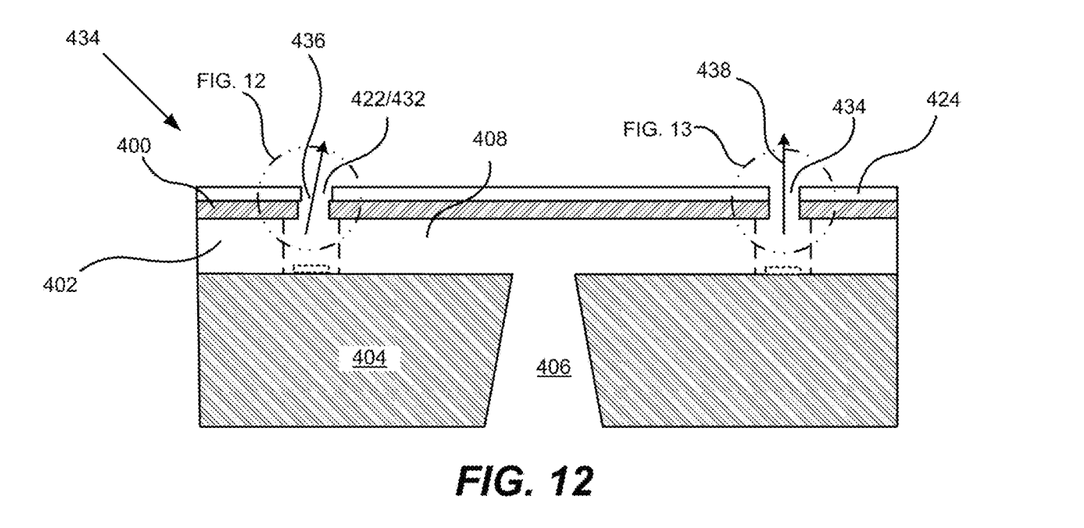
FIG. 12 is a schematic cross-sectional view, not to scale, of the ejection head made by the process illustrated in FIGS. 6-9.
Figure 13:
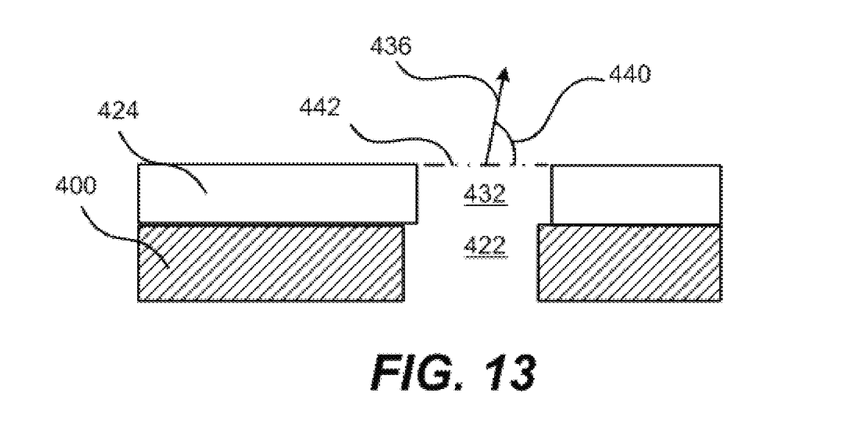
FIGS. 13 and 14 are elarged views, not to scale, of portions of the ejection head of FIG. 11.
Figure 14:
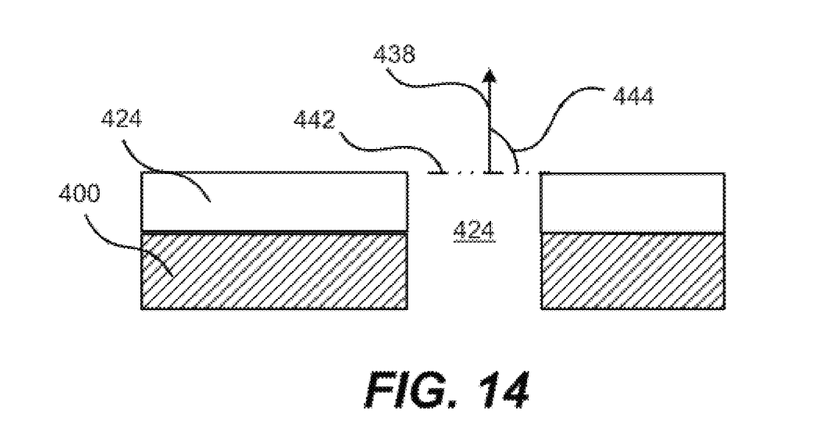

FIG. 1 is a cross sectional view, not to scale, of anatomy of a nasal cavity 10 of a person. A portion of the brain 14 is shown above the nasal cavity 10. An olfactory bulb 14 is disposed between the brain 12 and a cribriform plate 16. An olfactory mucosa is below the cribriform plate 16. The nasal cavity also includes a superior turbinate 20, a middle turbinate 22, respiratory mucosa 24 and an inferior turbinate 26. Item 28 represents the palate. Injection of a pharmaceutical drug mist enters the nasal cavity 10 through the nostrils 30 and squamous mucosa 32. In order to achieve proper delivery of drugs to the blood stream using a nasal spray device, the drugs must be delivered to the respiratory mucosa 24 which is highly vascularized. Two areas that are highly vascularized are the olfactory region and the respiratory region. The respiratory region contains turbinates which increase the surface area available for drug absorption.

It is believed that smaller, lower velocity fluid droplets are best for deposition of drugs in the nasal cavity 10. Fluid droplets with high inertia will tend to move in a straight line and land at the point only where they are aimed. Fluid droplets with low inertia will be affected by air resistance and air currents and are more likely to float throughout the nasal cavity for more even drug delivery coverage.

Another aspect of spray devices for the delivery of drugs that may increase deposition coverage is the plume angle of the fluid droplets. A wider plume angle is believed to provide greater mist formation and thus better coverage of drug delivery. Conventional methods for delivering drugs via the nasal cavity include medicine droppers, multi-spray bottles with spray tips, single-dose syringes with spray tips, and dry powder systems. Accordingly, conventional drug delivery devices are typically designed to deliver a specific drug to a nasal cavity and each device cannot be adapted for delivering a wide range of drugs via a nasal cavity route. Many of the conventional methods for nasal drug delivery rely on pressurized containers to inject a mist of fluid into the nasal cavity. Accordingly, the drug delivery devices are typically designed for a specific drug and cannot be adapted to administer a different drug.

Despite the availability of a variety of devices for delivering a mist of fluids, there remains a need for a fluid mist ejection device that can be tuned to deliver a variety of fluids over a range of velocities, fluid ejection times, and plume angles.

In view of the foregoing an embodiments of the disclosure provide a fluid jet ejection device, a method of making a fluid jet ejection head, and a method of improving the plume characteristics of fluid ejected from the fluid jet ejection head. The fluid jet ejection device includes a cartridge body; and a fluid jet ejection cartridge disposed in the cartridge body. The fluid jet ejection cartridge contains a fluid and an ejection head attached to the fluid jet ejection cartridge. The ejection head contains a plurality of fluid ejectors thereon and a nozzle plate having a plurality of fluid ejection nozzles therein associated with the plurality of fluid ejectors. At least one of the plurality of fluid ejection nozzles has an orthogonal axial flow path relative to a plane defined by the nozzle plate and at least one of the plurality of fluid ejection nozzles has an angled axial flow path relative to a plane define by the nozzle plate.

In another embodiment there is provided a method of making an ejection head. The method includes providing a semiconductor substrate having a plurality of fluid ejectors thereon. A fluid flow layer is applied to the semiconductor substrate. Fluid channels and fluid chambers are imaged and developed in the fluid flow layer. A fluid supply via is etched through the semiconductor substrate. A first nozzle plate layer is applied to the fluid flow layer. The first nozzle plate layer is imaged and developed to provide a first plurality of nozzle holes therein. A second nozzle plate layer is applied to the first nozzle plate layer. The second nozzle plate layer is imaged and developed to provide a second plurality of nozzle holes therein, wherein at least a portion of the second plurality of nozzle holes are offset from the first plurality of nozzle holes.

Another embodiment provides a method for improving plume characteristics of fluid ejected from a fluid jet ejection head. The method includes applying a first nozzle plate layer to a fluid flow layer on an ejection head substrate; imaging and developing the first nozzle plate layer to provide a first plurality of nozzle holes therein; applying a second nozzle plate layer to the first nozzle plate layer; imaging and developing the second nozzle plate layer to provide a second plurality of nozzle holes therein, wherein at least a portion of the second plurality of nozzle holes are offset from the first plurality of nozzle holes; and ejecting fluid from the ejection head through the first and second nozzle plate layers.

In some embodiments, the first nozzle plate layer and second nozzle plate layer comprise laminated photoresist material layers.

In some embodiments, the first nozzle plate layer is laminated to a flow feature layer for the ejection head.

In some embodiments, the first nozzle plate layer has a thickness ranging from about 5 to about 30 microns.

In some embodiments, the second nozzle plate layer has a thickness ranging from about 5 to about 30 microns.

In some embodiments, the angled axial flow path is provided by a second nozzle plate layer attached to a first nozzle plate layer.

In some embodiments, the portion of offset nozzle holes provides an angular discharge of fluid droplets relative to a plane defined by the second nozzle plate layer.

An advantage of the device described herein is that the device may be used for a wide variety of fluids having different fluid characteristics. The device may be operated to provide a variety of plume angles by alternately or simultaneously activating fluid ejectors to eject fluid from fluid ejection nozzles having orthogonal and angled fluid flow paths.

DETAILED DESCRIPTION

For the purposes of this disclosure, the following terms are defined:
a) plume means the randomly directed mist of fluid droplets with low inertia that are affected by air resistance and air currents and are likely to float throughout a nasal chamber for more even coverage;
b) plume angle is a measure of an angle of a cone-shaped volume of randomly directed mist of fluid droplets in the plume;
c) plume height is a measure of a total height of mist of fluid droplets in a plume measured from an outlet of a fluid ejection head to a total travel distance of the plume;

d) fluid jet length is a measure of a length of high inertia fluid droplets ejected from an outlet of an ejection head to the apex of the plume angle;

e) burst is defined as the number of times a fluid droplet is ejected from an individual nozzle. A burst of fluid occurs when a fluid ejector is fired by a series of voltage pulses of sufficient magnitude to eject fluid through an associated nozzle;

f) burst length is defined as the total number of times each of the fluid ejectors is fired per burst;

g) burst delay is defined as amount of time between individual bursts; and h) offset nozzle holes means that a center of a nozzle hole in a first nozzle plate layer is offset a predetermined amount from a center of a nozzle hole in an adjacent second nozzle plate layer An illustration of fluid jet ejection device 100 is illustrated in a cross-sectional view, not to scale, in FIG. 2. The device includes a cartridge body 102, having a fluid outlet nozzle 104 attached to the cartridge body 102. A fluid jet ejection cartridge 106 is disposed in the cartridge body 102. The fluid jet ejection cartridge 106 contains a fluid to be dispensed by the device 100. A logic board 108 is disposed in cartridge body 102 and is electrically connected via a logic board connector 110 to an ejection head 112 on the fluid jet ejection cartridge 106. As described in more detail below, the ejection head 112 includes plurality of fluid ejection nozzles and associated fluid ejectors. A processor 114 is disposed on the logic board 108 or on the ejection head 112 for executing a control algorithm to control the ejection head 112 to modify plume characteristics of fluid ejected from the ejection head by controlling which fluid ejectors are activated. The cartridge body 102 may include a rechargeable battery 116 electrically connected to the logic board 108 for providing power to the ejection head 112. A power switch 118 is used to activate the device 100. A USB input 120 may also be included to reprogram the processor for use with different pharmaceutical fluids. An activation button 122 may be used to initiate delivery of fluid droplet mist on-demand by a user.

A wide variety of ejection heads 112 may be used with the device 100 described above. Accordingly, the ejection head 112 may be selected from a thermal jet ejection head, a bubble jet ejection head, or a piezoelectric jet ejection head. Each of the foregoing ejection heads can produce a spray of fluid on demand and may be programmed to provide a variety of fluid plume characteristics as described below.

Unlike conventional inkjet ejection heads which are designed to eject fluid droplets in a straight line for 2 to 3 mm to reach a substrate such as paper, the device 100 described herein is designed to eject fluid droplets as a mist further into an air stream. When the fluid jet ejection device 100 is used as a nasal spray device, the mist of fluid droplets preferably land in the mucosa area of the nasal cavity. FIG. 3 is a schematic illustration of fluid jet ejection device 200 having an ejection head 202 for ejecting fluid therefrom to form a relatively high velocity fluid jet stream 204 and a low velocity plume 206 of fluid mist that floats on ambient air currents. The plume 206 characteristics, such as plume height PH and plume angle PA as well as the fluid jet stream length IL may be affected by how the ejection head 202 is operated. For example, a wider plume 206 may be the result of collisions between droplets as they are ejected from the ejection head 202. Another characteristics that effects the plume 206 is the entrainment of fluid droplets from the ejection head 202. High velocity fluid droplets tend to create an airflow perpendicular to the ejection head 202 which entrains subsequent droplets ejected from the ejection head 202 to draw the droplets further from the ejection head. 202. Accordingly, air entrainment can affect both the fluid jet stream 204 and the plume 206.

Without desiring to be bound by theoretical considerations, it is believed that the fluid droplet angle relative to a plane defined by the nozzle plate can affect the plume angle (PA). The angled fluid droplets are believed to interact in the air stream with other fluid droplets. The interaction of fluid droplets with different angular trajectories causes a wider plume angle. A wider plume angle is believed to provide greater mist formation for fluid droplet impact over a wider target area.

With reference to FIG. 4, there is illustrated a schematic cross-sectional view of an ejection head 300 having a single layer nozzle plate 302 with a thickness T attached to a flow feature layer 304. The flow feature layer 304 includes a fluid flow channel 306 for directing fluid from a fluid supply via 308 in a semiconductor substrate 310 to a fluid chamber 312. The fluid chamber 312 includes a fluid ejector 314 for ejecting fluid through a nozzle hole 316 in the nozzle plate 302. A flow path through the nozzle hole 316 is indicated by arrow 318 which is orthogonal to a plane defined by the surface 320 of the nozzle plate 302.

A plan view of the ejection head is illustrated in FIG. 5 illustrating a plurality of nozzle holes 316 disposed on both sides of the fluid supply via 308. The fluid ejectors can be activated simultaneously, sequentially, alternately, or in pre-determined groups to provide fluid droplets for mist formation as described above. Even if the fluid ejector parameters such as frequency, pulse width, burst length, or burst delay are modified, the modification ranges for these parameters for a conventional fluid ejection head may not enough to obtain the desired plume characteristics.

Accordingly, the disclosure provides an ejection head containing a plurality of nozzle holes wherein at least one nozzle hole has an orthogonal axial flow path length and at least one nozzle hole has an angled axial flow path length is provided. An ejection head 434 according to the disclosure is illustrated in FIG. 6. By combining one or more nozzle holes 422/432 having an angled axial flow path (arrow 436) with one or more nozzle holes 434 have an orthogonal axial flow path (arrow 438), interaction between droplets ejected from the ejection head is increased thereby producing a wider plume angle. The orthogonal axial flow nozzles 434 and the angled axial flow nozzles 422/432 can be adjacent to one another or on opposite sides of the fluid supply via 406 and may be activated simultaneously, sequentially, alternately, or in pre-determined groups to produce increased interaction between fluid droplets in the air stream.

The ejection head according to the disclosure is made by applying a first nozzle plate layer 400 to a flow feature layer 402 that is attached to a semiconductor substrate 404 as shown in FIG. 7. The flow feature layer 402 is a photoimageable material, such as a negative photoresist material, that is spin coated or laminated to the semiconductor substrate 404 prior to forming a fluid supply via 406 in the semiconductor substrate 404. The flow feature layer 402 includes a fluid flow channel 408 for directing fluid from the fluid supply via 406 to a fluid chamber 410 that includes a fluid ejector 412 and may have a thickness ranging from about 10 to about 60 microns. Once the fluid chamber 410 and fluid flow channel 408 are imaged and developed in the flow feature layer 402, and the fluid supply channel is etched through the semiconductor substrate 404, the first nozzle plate layer 400 is laminated to the flow feature layer 402. The first nozzle plate layer 400 may have a thickness ranging from about 5 to about 30 microns and may be a photoimageable material such as a negative photoresist material.

In the next step of the process, as shown in FIG. 8, a mask 414 having opaque areas 416 and transparent areas 418 is used to image nozzle holes having the first axial flow path length in the first nozzle layer 400 using actinic radiation such as ultraviolet (UV) light indicated by arrows 420. After imaging the first nozzle plate layer 400, the first nozzle plate layer is developed to provide the nozzle holes 422.

In FIG. 9, a second nozzle plate layer 424 is laminated to the first nozzle plate layer 400. Like the first nozzle plate layer 400, the second nozzle plate layer may be a negative photoresist material having a thickness ranging from about 5 to about 30 microns. Next, a mask 426 containing opaque areas 428 and transparent areas 430 is used to image nozzle holes in the second nozzle plate layer 424 (FIG. 10). As shown in FIG. 11, the center of nozzle holes 422 in the first nozzle plate layer 400 are offset from the center of nozzle holes 432 in the second nozzle plate layer 424. However, the centers of some of the nozzle holes 434 in both the first nozzle plate layer 400 and the second nozzle plate layer 424 coincide so that there is no offset. As shown in FIG. 12, the offset nozzle holes 422/432 cause fluid to be ejected from the nozzle holes 422/432 at an angle as shown by arrow 436. FIG. 12 also shows a nozzle hole 434 wherein fluid is ejected orthogonal to a plane defined by the combined nozzle plate layers 400 and 424 as illustrated by arrow 438. FIGS. 13 and 14 are enlarged views of the nozzle holes 432/422 and 434. The angle 440 in FIG. 13 may range from about 45 degrees to about 89 degrees with respect to a plane 442 defined by the nozzle plate layers 400 and 424. In FIG. 14, the angle 444 is 90 degrees with respect to the plane 442.

The photoresist materials that may be used for making the first and second nozzle plate layers 400 and 424 typically contain photoacid generators and may be formulated to include one or more of a multi-functional epoxy compound, a di-functional epoxy compound, a relatively high molecular weight polyhydroxy ether, an adhesion enhancer, an aliphatic ketone solvent, and optionally a hydrophobicity agent. For purposes of the disclosure, "difunctional epoxy" means epoxy compounds and materials having only two epoxy functional groups in the molecule. "Multifunctional epoxy" means epoxy compounds and materials having more than two epoxy functional groups in the molecule.

An epoxy component for making a photoresist formulation according to the disclosure, may be selected from aromatic epoxides such as glycidyl ethers of polyphenols. An exemplary first multi-functional epoxy resin is a polyglycidyl ether of a phenolformaldehyde novolac resin such as a novolac epoxy resin having an epoxide gram equivalent weight ranging from about 190 to about 250 and a viscosity at 130° C. ranging from about 10 to about 60.

The multi-functional epoxy component may have a weight average molecular weight of about 3,000 to about 5,000 Daltons as determined by gel permeation chromatography, and an average epoxide group functionality of greater than 3, preferably from about 6 to about 10. The amount of multifunctional epoxy resin in a photoresist formulation may range from about 30 to about 50 percent by weight based on the weight of the dried photoresist layer.

The di-functional epoxy component may be selected from di-functional epoxy compounds which include diglycidyl ethers of bisphenol-A, 3,4-epoxycyclohexylmethyl-3,4-epoxycyclo-hexene carboxylate, 3,4-epoxy-6-methylcyclohexylmethyl-3,4-epoxy-6-methylcy-clohexene carboxylate, bis(3,4-epoxy-6-methylcyclohexylmethyl) adipate, and bis(2,3-epoxycyclopentyl) ether.

An exemplary di-functional epoxy component is a bisphenol-A/epichlorohydrin epoxy resin having an epoxide equivalent of greater than about 1000. An "epoxide equivalent" is the number of grams of resin containing 1 gram-equivalent of epoxide. The weight average molecular weight of the di-functional epoxy component is typically above 2500 Daltons, e.g., from about 2800 to about 3500 weight average molecular weight. The amount of the first di-functional epoxy component in a photoresist formulation may range from about 30 to about 50 percent by weight based on the weight of the cured resin.

Exemplary photoacid generators include compounds or mixture of compounds capable of generating a cation such as an aromatic complex salt which may be selected from onium salts of a Group VA element, onium salts of a Group VIA element, and aromatic halonium salts. Aromatic complex salts, upon being exposed to ultraviolet radiation or electron beam irradiation, are capable of generating acid moieties which initiate reactions with epoxides. The photoacid generator may be present in the photoresist formulations described herein in an amount ranging from about 5 to about 15 weight percent based on the weight of the cured resin.

Compounds that generate a protic acid when irradiated by active rays, may be used as the photoacid generator, including, but are not limited to, aromatic iodonium complex salts and aromatic sulfonium complex salts. Examples include di-(t-butylphenyl)iodonium triflate, diphenyliodonium tetrakis(pentafluorophenyl)borate, diphenyliodonium hexafluorophosphate, diphenyliodonium hexafluoroantimonate, di(4-nonylphenyl)iodonium hexafluorophosphate, [4-(octyloxy)phenyl]phenyliodonium hexafluoroantimonate, triphenylsulfonium triflate, triphenyl-sulfonium hexafluorophosphate, triphenylsulfonium hexafluoroantimonate, triphenylsulfonium tetrakis(pentafluorophenyl)borate, 4,4'-bis[diphenylsulfonium]diphenylsulfide, bis-hexafluoro-phosphate, 4,4'-bis[di([beta]-hydroxyethoxy) phenylsulfonium]diphenylsulfide bis-hexafluoro-antimonate, 4,4'-bis[di([beta]-hydroxyethoxy) (phenylsulfonium)diphenylsulfide-bishexafluoro-phosphate 7-[di(p-tolyl)sulfonium]-2-isopropylthioxanthone hexafluorophosphate, 7-[di(p-tolyl)sulfonio-2-isopropylthioxanthone hexafluoroantimonate, 7-[di(p-tolyl)sulfonium]-2-isopropyl tetrakis(pentafluorophenyl)borate, phenylcarbonyl-4'-diphenylsulfonium diphenyl-sulfide hexafluorophosphate, phenylcarbonyl-4'-diphenylsulfonium diphenylsulfide hexafluoroantimonate, 4-tert-butylphenylcarbonyl-4'-diphenylsulfonium diphenylsulfide hexafluorophosphate, 4-tert-butylphenylcarbonyl-4'-diphenylsulfonium diphenylsulfide hexafluoroantimonate, 4-tert-butylphenylcarbonyl-4'-diphenylsulfonium diphenylsulfide tetrakis(pentafluorophenyl)borate, diphenyl [4-(phenylthio) phenyl] sulfonium hexafluoro-antimonate and the like.

A solvent for use in preparing photoresist formulations is a solvent which is non-photoreactive. Non-photoreactive solvents include, but are not limited gamma-butyrolactone, $C_{1-6}$ acetates, tetrahydrofuran, low molecular weight ketones, mixtures thereof and the like. The non-photoreactive solvent is present in the formulation mixture used to provide the nozzle plate layers 400 and 424 in an amount ranging from about 20 to about 90 weight percent, such as from about 40 to about 60 weight percent, based on the total weight of the photoresist formulation. The non-photoreactive solvent typically does not remain in the cured composite film layer and is thus removed prior to or during the composite film layer curing steps.

The photoresist formulation may optionally include an effective amount of an adhesion enhancing agent such as a silane compound. Silane compounds that are compatible with the components of the photoresist formulation typically have a functional group capable of reacting with at least one member selected from the group consisting of the multi-functional epoxy compound, the difunctional epoxy compound and the photoinitiator. Such an adhesion enhancing agent may be a silane with an epoxide functional group such as 3-(guanidinyl)propyltrimethoxysilane, and a glycidoxyalkyltrialkoxysilane, e.g., gamma-glycidoxypropyltrimethoxysilane. When used, the adhesion enhancing agent can be present in an amount ranging from about 0.5 to about 2 weight percent, such as from about 1.0 to about 1.5 weight percent based on total weight of the cured resin, including all ranges subsumed therein. Adhesion enhancing agents, as used herein, are defined to mean organic materials soluble in the photoresist composition which assist the film forming and adhesion characteristics of the photoresist materials.

Another optional component that may be used in the photoresist formulations for the nozzle plate layers includes a hydrophobicity agent. The hydrophobicity agent that may be used includes silicon containing materials such as silanes and siloxanes. Accordingly, the hydrophobicity agent may be selected from heptadecafluorodecyltrimethoxysilane, octadecyldimethylchlorosilane, ocatadecyltricholorsilane, methytrimethoxysilane, octyltriethoxysilane, phenyltrimethoxysilane, t-butylmethoxysilane, tetraethoxysilane, sodium methyl siliconate, vinytrimethoxysilane, N-(3-(trimethoxylsilyl)propyl)ethylenediamine polymethylmethoxysiloxane, polydimethylsiloxane, polyethylhydrogensiloxane, and dimethyl siloxane. The amount of hydrophobicity agent in the photoresist layers 400 and 424 may range from about 0.5 to about 2 weight percent, such as from about 1.0 to about 1.5 weight percent based on total weight of the cured resin, including all ranges subsumed therein.

While the foregoing disclosure provides nozzle plate layers 400 and 424 made of photoresist materials, the first and second nozzle plate layers are not limited to photoresist material layers. Other materials such as polyimide materials may be used to provide the first and second nozzle plate layers 400 and 424 and nozzle holes therein as described above.

It is noted that, as used in this specification and the appended claims, the singular forms "a," "an," and "the," include plural referents unless expressly and unequivocally limited to one referent. As used herein, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A fluid jet ejection device comprising:
a cartridge body;
a fluid outlet nozzle attached to the cartridge body;
a fluid jet ejection cartridge disposed in the cartridge body, the fluid jet ejection cartridge containing a fluid and an ejection head attached to the fluid jet ejection cartridge; wherein the ejection head contains a plurality of fluid ejectors thereon and a nozzle plate having a plurality of fluid ejection nozzles therein associated with the plurality of fluid ejectors, wherein at least one of the plurality of fluid ejection nozzles has an orthogonal axial flow path relative to a plane defined by the nozzle plate and at least one of the plurality of fluid ejection nozzles has an angled axial flow path relative to a plane define by the nozzle plate, wherein the angled axial flow path is configured to increase interaction between fluid droplets and is provided by a second nozzle plate layer attached to a first nozzle plate layer and wherein the first nozzle plate layer and second nozzle plate layer comprise laminated photoresist material layers.

2. The fluid jet ejection device of claim 1, wherein the first nozzle plate layer has a thickness ranging from about 5 to about 30 microns.

3. The fluid jet ejection device of claim 1, wherein the second nozzle plate layer has a thickness ranging from about 5 to about 30 microns.

4. The fluid jet ejection device of claim 1, wherein the first nozzle plate layer is laminated to a flow feature layer for the ejection head.

5. A method of making an ejection head, the method comprising:
providing a semiconductor substrate having a plurality of fluid ejectors thereon;
applying a fluid flow layer to the semiconductor substrate;
imaging and developing fluid channels and fluid chambers in the fluid flow layer;
etching a fluid supply via through the semiconductor substrate;
laminating a first photoresist nozzle plate layer to the fluid flow layer;
imaging and developing the first photoresist nozzle plate layer to provide a first plurality of nozzle holes therein;
laminating a second photoresist nozzle plate layer to the first photoresist nozzle plate layer;
imaging and developing the second photoresist nozzle plate layer to provide a second plurality of nozzle holes therein, wherein at least a portion of the second plurality of nozzle holes are offset from the first plurality of nozzle holes.

6. The method of claim 5, wherein the first photoresist nozzle plate layer has a thickness ranging from about 5 to about 30 microns.

7. The method of claim 5, wherein the second photoresist nozzle plate layer has a thickness ranging from about 5 to about 30 microns.

8. The method of claim 5, wherein the portion of offset nozzle holes provides an angular discharge of fluid droplets relative to a plane defined by the second photoresist nozzle plate layer.

9. A method for improving plume characteristics of fluid ejected from a fluid jet ejection head, comprising:
laminating a first photoresist nozzle plate layer to a fluid flow layer on an ejection head substrate;
imaging and developing the first photoresist nozzle plate layer to provide a first plurality of nozzle holes therein;
laminating a second photoresist nozzle plate layer to the first photoresist nozzle plate layer;
imaging and developing the second photoresist nozzle plate layer to provide a second plurality of nozzle holes therein, wherein at least a portion of the second plurality of nozzle holes are offset from the first plurality of nozzle holes; and
ejecting fluid from the ejection head through the first and second photoresist nozzle plate layers.

10. The method of claim 9, wherein the first photoresist nozzle plate layer has a thickness ranging from about 5 to about 30 microns.

11. The method of claim 9, wherein the second photoresist nozzle plate layer has a thickness ranging from about 5 to about 30 microns.

* * * * *